Figure 1:
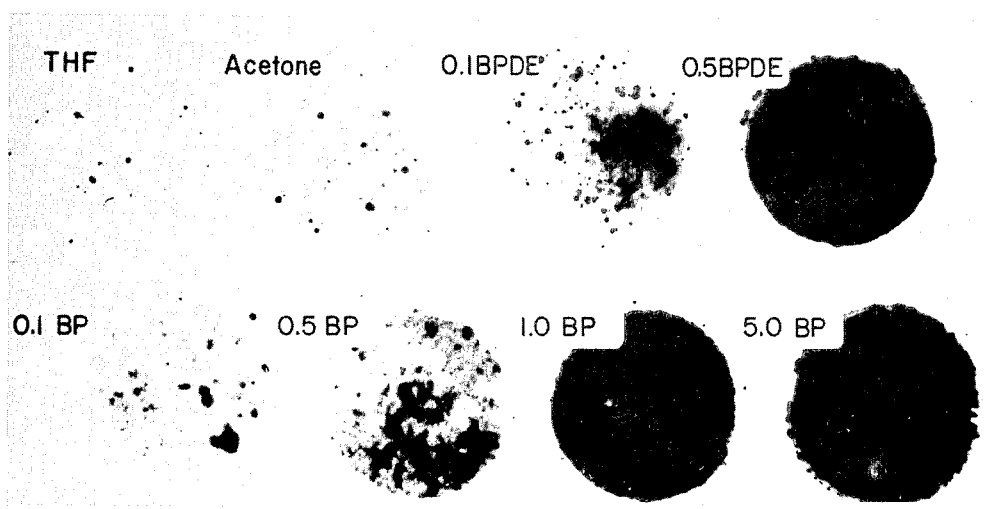

United States Patent [19]

Lavi

[11] Patent Number: 4,532,220
[45] Date of Patent: Jul. 30, 1985

[54] ASSAYS FOR THE DETERMINATION OF CARCINOGENICITY

[75] Inventor: Sara Lavi, Kiryat Ono, Israel

[73] Assignee: Yeda Research and Development Company Ltd., Rehovot, Israel

[21] Appl. No.: 361,061

[22] Filed: Mar. 23, 1982

[30] Foreign Application Priority Data

Mar. 25, 1981 [IL]  Israel ......................................... 62479

[51] Int. Cl.$^3$ .......................... C12N 15/00; C12Q 1/68; G01N 33/50
[52] U.S. Cl. ..................................... 436/501; 436/504; 436/63; 436/64; 436/94; 436/804; 436/808; 436/813; 435/6; 435/29; 435/172.2; 435/810; 935/6
[58] Field of Search ..................... 424/1, 1.5; 436/501, 436/504, 63, 64, 94, 804, 808, 813; 435/6, 29, 91, 172, 270, 810, 5, 235, 240, 948

[56] References Cited

U.S. PATENT DOCUMENTS

| | | | |
|---|---|---|---|
| 4,066,510 | 1/1978 | Thilly et al. | 435/6 |
| 4,072,574 | 2/1978 | Loeb et al. | 435/6 |
| 4,264,729 | 4/1981 | Beljanski | 435/6 |
| 4,299,915 | 11/1981 | Thilly et al. | 435/6 |
| 4,302,535 | 11/1981 | Skopek et al. | 435/6 |
| 4,345,026 | 8/1982 | Lew | 435/6 |
| 4,352,880 | 10/1982 | Awerbuch | 435/6 |

OTHER PUBLICATIONS

Pall, Martin L., Proc. Natl. Acad. Sci. USA, vol. 78, No. 4, pp. 2465-2468, (4-1981).
Lavi, S., *Proc. National Academy of Sciences*, vol. 78(10), pp. 6144-6148, (10/1981), "Carcinogen-mediated ...".
Winocour and Keshet, Proc. National Academy of Sciences, vol 77(8), pp. 4861-4865, (8/1980), "Indiscriminate ...".
Sarasin and Hanawalt, Proc. National Academy Sciences, vol. 75(1), pp. 346-350, (1/1978), "Carcinogens ...".
Krieg et al., *Virology*, vol. 108, pp. 453-461, (1/1981), "The Integrated SU40 Genome ...".
Blakeslee, J. R. et al., Proc. Amer. Assoc. Cancer Research, vol. 15, p. 129, #516, (1974).
Wolff, G. L., J. Environmental Pathology and Toxicology, vol. 1(2), pp. 79-90, (1977).
Schemke, R. T., ed., *Gene Amplification*, Cold Spring Harbor Laboratory, (1982).
*Gene Amplification and Analysis*, Chirilgian, J. G., Papas, T. S., eds., Elsevier/North Holland, vols. 1,2, (1980,1981).
Hollstein, M. et al., Mutation Research, vol. 65, pp. 133-226, (1979).
D'Ambroso, S. M. et al., Proc. Natl. Acad. Sci., vol. 73, pp. 2396-2400, (1976).
Todaro, G. J. et al., Proc. Natl. Acad. Sci., vol. 69, pp. 1009-1015, (1972).
Castro, B. C., Cancer Research, vol. 34, pp. 72-78, (1974).

*Primary Examiner*—Benjamin R. Padgett
*Assistant Examiner*—M. Moskowitz
*Attorney, Agent, or Firm*—Browdy and Neimark

[57] ABSTRACT

There is provided an assay for the determination of the carcinogenicity of chemical and physical agents, by exposing a selected line of tumor virus transformed cells to the agent to be tested and determining whether such exposure induces endogenous viral DNA replication in such cells, which induction is indicative of the carcinogenicity of the tested agent by in situ hybridization. There is provided a kit for carrying out such assay.

18 Claims, 5 Drawing Figures day 2   day 3   day 4   day 5

Control

DMBA $5 \times 10^5$ $5 \times 10^4$ $5 \times 10^3$

ASSAYS FOR THE DETERMINATION OF CARCINOGENICITY

FIELD OF THE INVENTION

The present invention relates to a novel assay for the determination of carcinogenicity of various substances and to means for carrying out such assays.

The novel assay is applicable to a variety of chemical and physical carcinogens and makes possible a rapid and effective screening for carcinogenicity.

BACKGROUND OF THE INVENTION

Although 80% of human cancer is the result of exogenous environmental agents, very little is known about the molecular mechanism(s) leading to carcinogenicity. Although carcinogenesis might be initiated by a mutational change, it cannot be described by a single mutational event because secondary stages must occur.

Massive changes in the organization of the genomic sequences by relocation and amplification of specific cellular sequences may be a critical step in carcinogenesis.

The design of new short-term bioassays for chemical carcinogens is of current interest. A number of short-term methods for detecting potential chemical carcinogens and mutagens have emerged from diverse areas of cancer research, genetic and molecular biology (Hollstein, M., McCann, J., Angelosanto, F. A. and Nichols, W. W. Mutation Res. 65, 133-226 (1979)).

Because no single assay has yet detected all the carcinogens, a variety of different tests may be required. None of the existing tests for carcinogenicity measure amplification or rearrangement of specific cellular sequences.

Recent studies in our laboratory on the carcinogen-mediated amplification of genomic sequences led us to the development of a model experimental system based on SV40 transformed Chinese hamster embryo cells and a highly sensitive in situ hybridization procedure for the detection of single cells in which viral DNA synthesis is induced.

This procedure enables the determination of the extent of the carcinogen mediated amplification of SV40 DNA sequences. The molecular mechanism leading to this phenomenon is currently unknown. The possibility that the amplification of SV40 DNA sequences is a reflection of a general gene amplification phenomenon is currently being investigated.

SUMMARY OF THE INVENTION

According to the present invention there is provided a novel assay for carcinogenic compounds and physical carcinogens, which makes possible the rapid and effective screening of chemical and physical carcinogens. The invention further relates to means for carrying out such tests and to kits for this purpose. The novel assay is based on the induction of endogenous viral DNA replication in selected lines of tumor virus transformed cells. Various types of cells can be transformed by tumor viruses, and such cell lines can be used for the novel assay. The invention is illustrated with reference to selected lines of SV40-transformed Chinese hamster cells. Exposure to carcinogens results in the induction of endogenous viral DNA replication. The induction is carcinogen dose dependent, and it does not take place with non-carcinogenic substances. The induction is sensitive to inhibitors of polycyclic hydrocarbon metabolism when precarcinogens requiring metabolic activation are used.

Amongst the various cell lines investigated, the most promising is the carcinogen-mediated induction of viral DNA synthesis in SV40-transformed lines of Chinese hamster cells. The novel assay is based on the observation that exposure of SV40-transformed lines of Chinese hamster cells to a variety of chemical and physical carcinogens leads to the induction of SV40 DNA synthesis in a high proportion of the cells. The cells induced for SV40 DNA synthesis are easily detected by sensitive in situ hydridization procedures. Experiments have shown that when non-carcinogenic substances are used, no such effects take place. Amongst the various possible cell lines which can be used for assays of this type, SV40-transformed Chinese hamster embryo cells were selected as they were found to be capable of metabolizing several chemical carcinogens into active intermediates and they were sufficiently permissive for SV40 DNA replication so that the induction process can be easily monitored in the carcinogen treated culture without the additional complication of cell fusion with fully permissive monkey cells.

The assay for cells induced to synthesize viral DNA is based upon in situ hybridization with a radioactive SV40 DNA probe. Two variations of the protocol were devised:

a. Dispersed cell assay
b. Disc cell assay a. Dispersed Cell Assay

In this assay the carcinogen was added to liquid culture medium. At various times following exposure, the cells were trypsinized, counted and known numbers of surviving cells were trapped on nitrocellulose membrane filters which were then hybridized with $^{32}P$-SV40 DNA probe. (Winocour, E. and Keshet, I., in preparation and Winocour, E. and Keshet, I. Proc. Natl. Acad. Sci. USA 77-4861-4865 (1980)). The results of this hybridization can be visualized by autoradiography and can be quantified by counting the filters in scintillation counters.

The cell line used for these studies, CO50, is a clonal isolate derived from Chinese hamster embryo cells after infection with SV40 DNA, and plating in soft agar. Cell line CO50 has been deposited at the Institute Pasteur in Paris, France and has been assigned deposit number I-188. Exposure of CO50 cells to chemical carcinogens such as benzo [a]pyrene (BP) or its active metabolite benzo [a]pyrene 7,8-diol-9,10 epoxide (BPDE)(Huberman, E., Sachs, L., Young, S. K. and Gelboin, H. V. Proc. Natl. Acad. Sci USA 73, 607-611 (1976 and Sims, P., Grover, P. L., Swisland A., Pal, K. and Hewer, A. Nature 252, 326-327 (1974)) induced increasing levels of SV40 DNA synthesis, as described and illustrated in FIG. 1. Both carcinogens were toxic to the cells but there was no direct relationship between the levels of SV40 DNA synthesis and the toxicity. A similar degree of induction of SV40 DNA synthesis was obtained when the cells were treated with 5 μg/ml BP or 0.5 μg BPDE, but while 57% of the cells survived BP treatment, only 3% survived treatment with BPDE (data not shown). The finding that BP induced SV40 DNA synthesis in the same manner as the ultimate carcinogen BPDE implies that BP is converted to its active form BPDE which is responsible for the induction of SV40 DNA synthesis. To explore this possibility further, CO50 cells were treated with an inhibitor of polycyclic hydrocarbon metabolism (7,8 benzo-flavone)(Diamond, L. and Gelboin, H. V. Science 166. 1023–1025 (1969)) prior to BP application. Induction of SV40 DNA synthesis was completely inhibited as a result of this treatment (FIG. 2), demonstrating that metabolic activation of BP is required for the induction of SV40 DNA synthesis by BP. Pretreatment of the cells with BF also abolished the toxic effect of BP (data not shown).

Figure 3:
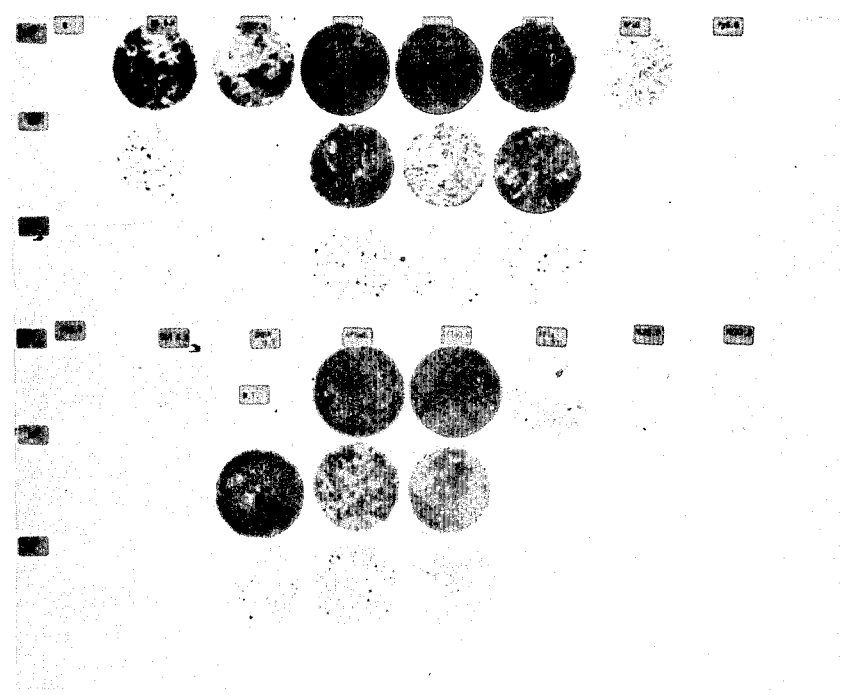

To determine the relationship between carcinogenicity and induction of SV40 DNA synthesis, CO50 cells were treated with a series of physical and chemical carcinogens including activation-dependent and activation-independent varieties, as well as with noncarcinogenic polycyclic hydrocarbons. As seen in FIG. 3 and Table 1, SV40 DNA synthesis was induced by both chemical and physical carcinogens, while noncarcinogenic compounds, like DMSO, pyrene (Py), phenanthrene (Ph) and dibenz(a,c) anthracene (DBA) were inactive according to this assay. Induction of SV40 DNA synthesis in variable degrees was obtained when the tester cells were treated either by activation-independent carcinogens like N-methyl-N'-nitro-N-nitrosoguanidine (NG) and ethyl methanesulfonate (EMS) or by activation-dependent carcinogens like BP, 9, 10 dimethylbenzanthracene (DMBA), aflatoxin Bl (Afl) 3-methylcholanthrene (MCA) and 4-nitroquinoline 1-oxide (4NQO), or when the cells were irradiated by $\gamma$ or U.V. irradiation. Treatment of the cells with EMS (1.0 $\mu$g/ml), DMBA (1 $\mu$g/ml), Alf (0.1 and 0.01 $\mu$g/ml) or with $\gamma$ or U.V. irradiation, was followed by a dramatic induction of SV40 DNA synthesis which could be monitored even when $10^4$ cells were assayed, indicating that induction occurred in a substantial number of cells. There was a positive relationship between the concentration of the carcinogens which were tested, and the intensity of SV40 DNA induction. Increasing concentrations of BP (0.1–5.0 $\mu$g/ml), BPDE (0.1 and 0.5 $\mu$g/ml)(FIG. 1) or Alf (0.001–0.10 $\mu$g/ml)(FIG. 3 and Table 1) induced increased synthesis of SV40 DNA. As seen in Table 1, induction of SV40 DNA synthesis was followed by reduced survival of the treated cells. Noncarcinogenic compounds were not toxic to the cells and did not induce SV40 DNA synthesis in the tested cells.

Figure 4:
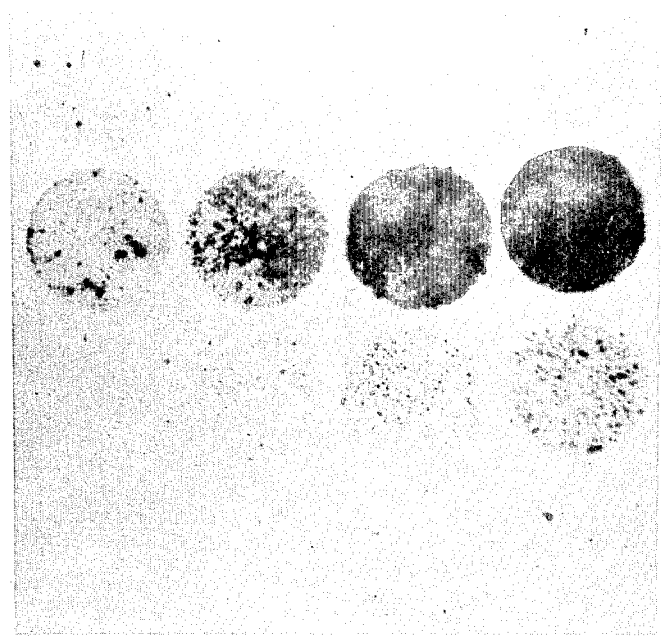

Experiments were performed to determine the optimal time for the induction of SV40 DNA synthesis in CO50 cells. As seen in FIG. 4, synthesis could be observed as soon as two days after treatment with DMBA (0.1 $\mu$g/ml). Thereafter, SV40 DNA synthesis increases and maximal induction is observed 4–5 days after treatment.

The design and possible implementation of novel short-term bioassays for chemical carcinogens is of great interest. A number of short-term testing methods for detecting potential chemical carcinogens and mutagens have emerged from diverse areas of cancer research, genetic and molecular biology (Hollstein, M., McCann, J., Angelosanto, F. A. and Nichols, W. W. Mutation Res. 65, 133–226 (1979)). Because no single assay has yet detected all carcinogens, the necessity for a battery of tests seems clear. Carcinogen-mediated induction of SV40 DNA synthesis could be used as a potential short-term test in a battery of screening tests for chemical carcinogens. This assay has the advantage that (a) the tester cells are eukaryotic cells capable of metabolizing carcinogens; (b) induction of SV 40 DNA synthesis, the end point in this assay, is closely related to the carcinogenic activity of the tested compounds; (c) large fractions of the cells used for the assay respond to the treatment with the carcinogens and, therefore, the carcinogen-mediated induction of SV40 DNA synthesis can be measured at the biochemical level; (d) this assay can monitor the toxicity of the compounds which are tested; and (e) the assay is rapid and reproducible.

b. Disc Cell Assay

Figure 5:
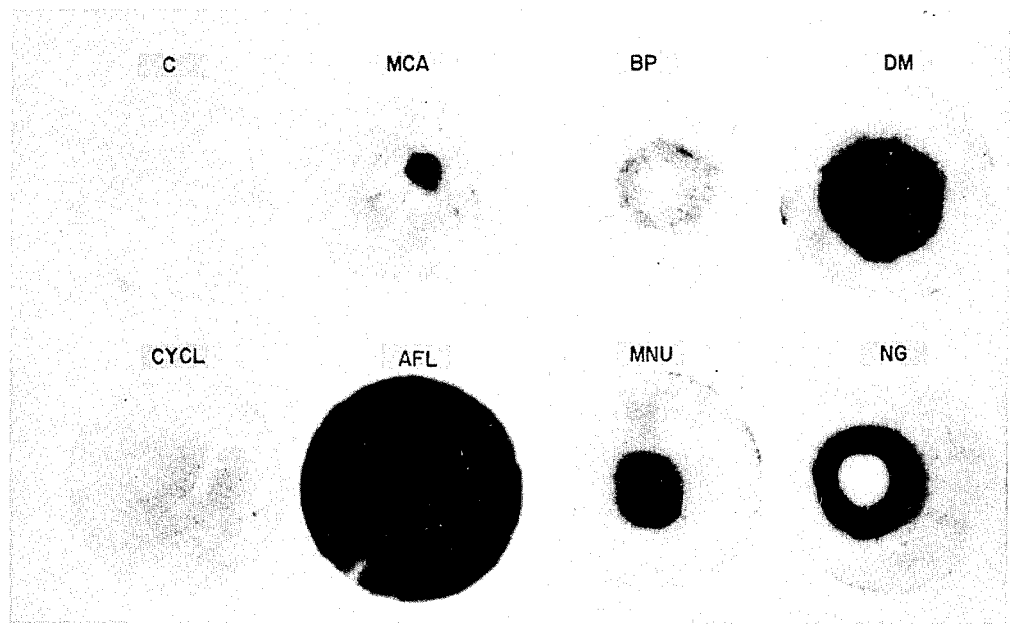

The induction potential of several carcinogens was also evaluated by a disc test. In this assay, a paper disc containing the compound under test is placed on top of the agar overlaying the CO50 cells. Four days later, the agar overlay is removed and the cell monolayer is transferred to nitrocellulose filter and then hybridized against [$^{32}$P]-SV40 DNA. As shown in FIG. 5, treatment of CO50 cells with 3-methylcholanthrene (MCA), or BP, or DMBA, or Aflatoxin Bl (AFL), or methylnitrosourea (MNU), or MNNG (NG), or Cyclophosphamide (Cycl) resulted in an induction of SV40 DNA synthesis to different degrees. While aflatoxin Bl induced SV40 DNA synthesis throughout the whole monolayer, cyclophosphamide elicitated a weak response. MNNG was toxic and yielded a ring of dead cells around the disc followed by a ring of cells induced for SV40 DNA synthesis. BP was toxic to the cells and produced a similar "clear zone" of dead cells followed by a ring of cells induced for SV40 DNA synthesis (but the intensity of SV40 DNA induction was lower than that obtained by MNNG). DMBA was found to be an efficient inducer and less toxic to the cells. MNU and 3-MCA were weaker inducers and cyclophosphamide was found to be a particularly weak inducer under this assay. The different responses may reflect either (a) differences in the diffusion rates of the compounds through the agar, (b) variations in compound stability, or (c) inherent differences in the carcinogenic potential of the various compounds.

LEGEND TO FIGURES

FIG. 1: Benzo[a]pyrene (BP) and benzo[a]pyrene 7,8-diol-9,10 epoxide (BPDE) on the induction of SV40 DNA synthesis in SV40 transformed Chinese hamster cells $5 \times 10^5$ CO50 cells (I-188) in 4 ml of modified Eagle's medium containing 10% fetal calfserum were seeded. 24 hours thereafter, the appropriate concentration of the following compounds was added to 1 ml of medium.

BP (0.1–5.0 $\mu$g/ml as indicated in photographs); or BPDE (0.1 and 0.5 $\mu$g/ml); or tetrahydrofurane (THF 0.5%, the solvent for BPDE); or acetone (0.5%, the solvent for BP). After 5 days of exposure, the cell monolayer was disrupted with trypsin EDTA and the surviving cells were counted in a hemo-cytometer. Samples of $10^6$ cells (diluted in special PBS) were trapped on nitrocellulose membrane filters (Schleicher and Schull, 0.45 micrometer, 4 cm diameter) by filtration under vacuum (Winocour, E. and Keshet, I. In preparation). The filters, with the cells facing upwards, were placed for 1 minute on top of Whatmann 3 MM paper saturated with 0.5 N NaOH containing 1.5 M NaCl. The filters were then blotted dry and the alkali denaturation step, with intermittent drying, was repeated twice more. Finally, the filters, neutralized by three 1-minute contacts with Whatmann paper saturated with 1 M Tris-HCl (pH 7.0) and 2×SSC, were dried at room temperature and baked at 80° C. Hybridization against $^{32}$P SV40 DNA ($1 \times 10^8$ counts per minute/$\mu$g, 50,000 counts per minute/ml) was carried out as described by Winocour et al., (Winocour, E. and Keshet, I., Proc.-Natl.Acad.Sci. USA 77, 4861–4865 (1980)). The photograph shows an autoradiogram of the nitrocellulose membrane filters after hybridization with SV40 $^{32}$P DNA (autoradiographic exposure 24 hours at −70°C.).

Figure 2:
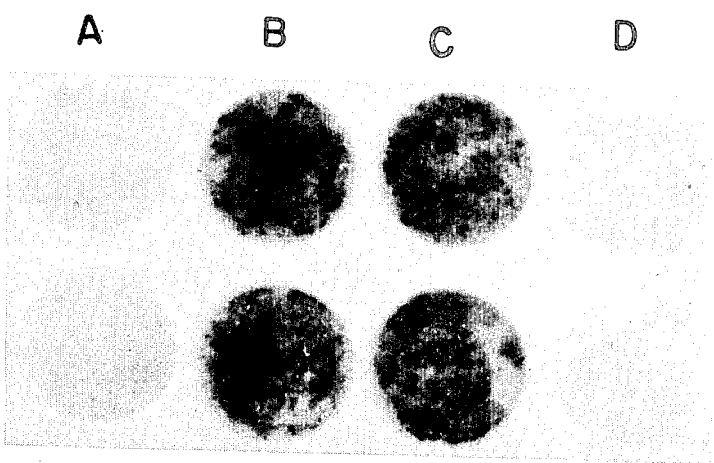

FIG. 2: Effect of 7,8 benzoflavone (BF) on the induction of SV40 DNA synthesis in CO50 cells treated with benzo[a]pyrene (BP) CO50 cells seeded at $5 \times 10^5$ cells (I-188) on 5 cm plates were treated 24 hours after seeding, as described in FIG. 1, with 0.5% acetone (a) or BP 1.0 (b) and 2.0 μg/ml (c) or 7,8 benzoflavone at 2.5 μg/ml which was added 2 hours prior to treatment with 1.0 μg/ml BP (d). After 4 days of treatment, the cells were trypsinized and $10^6$ cells were assayed for SV40 DNA synthesis, as described in legend to FIG. 1.

FIG. 3: Effect of potential carcinogens on the induction of SV40 DNA synthesis in SV40 transformed Chinese hamster cells $5 \times 10^5$ CO50 cells (I-188) were seeded on 5 cm plates. 24 hours after seeding the cells were treated as described in FIG. 1. The following compounds were applied for 24 hours: 0.5% DMSO (solvent for chemicals, C); N-methyl-N'-nitro-N-nitroso-guanidine (NG, 5 and 1 μg/ml); ethyl methanesulfonate (EMS, 1.0 μg/ml); benzo a pyrene (BP, 1 μg/ml), pyrene (Py, 10 μg/ml); phenanthrene (ph, 10 μg/ml); dibenzo (a,c) anthracene (DBA, 10 μg/ml); 9,10 dimethyl benzanthracene (DMBA, 0.1 μg/ml); aflatoxin B1 (Afl, 0.1, 0.01 and 0.001 μg/ml); 3-methylcholanthrene, (MCA, 5.0 μg/ml); 4-nitroquinoline 1-oxide (4NQO, 1.0 μg/ml) or irradiated with irradiation (250 R) or U.V. irradiation (50 J/m$^2$). Following the treatment the medium was replaced by fresh modified Eagle's medium containing 10% FCS. The cells were incubated for 4 additional days and the trypsinized samples of $10^6$, $10^5$ and $10^4$ cells (for DMBA only $10^5$ and $10^4$ cells) were analyzed by the dispersed cell assay for SV40 DNA synthesis as described in FIG. 1. The photograph shows an autoradiogram of nitrocellulose membrane filters after hybridization against $^{32}$P-SV40 DNA probe.

FIG. 4: Kinetics of SV40 DNA synthesis induced by DMBA in CO50 cells (I-188)

CO50 cells were treated with 0.5 μg/ml DMBA (control cells were treated with 0.5% DMSO, the solvent for DMBA) for 2–5 days as noted. The cells were then trypsinized and samples ($5 \times 10^5$ control cells, or $5 \times 10^5$, $5 \times 10^4$ or $5 \times 10^3$ treated cells as noted) were trapped on nitrocellulose filters, denatured and hybridized with $^{32}$P-SV40 DNA ($1 \times 10^8$ counts per minute/μg as described in FIG. 1 and in the text.

FIG. 5: The Disc Test

Cultures containing $2 \times 10^6$ CO50 cells (I-188) were overlayed with 0.9% agar. A 5 mm diameter disc of 3 MM paper (Whatmann) containing 10 μg of the compounds noted below were placed on top of the agar in the center of the plate. Four days later the disc and the agar overlay were removed, the cell monolayer was transferred to a nitrocellulose filter and the filters were hybridized as described elsewhere in the text. The photograph shows an autoradiogram of nitrocellulose membrane filters after hybridization against $^{32}$P-SV40 DNA ($1 \times 10^8$ counts per minute/μg, 50,000 counts per minute/ml). C, untreated control; MCA, 3-methyl-cholanthrene; BP, Benzo (a) pyrene, DM, 7, 12, dimethyl-benzanthracene; Cycl, cyclophosphamide; Afl, aflatoxin B1, MNU, nitrosomethyl urea; NG, N-methyl-N'-nitro-N-nitrosoguanidine.

TABLE 1

EFFECT OF POTENTIAL CARCINOGENS ON THE INDUCTION OF SV40 DNA SYNTHESIS IN CO50 CELLS[a]

| Treatment | | Surviving fraction[b] | CPM bound to[c] filters | CPM above control |
|---|---|---|---|---|
| DMSO, control. | 0.5% | 100 | 1,648 | — |
| MNNG | 5.0 μg/ml | 7 | 3,873 | 2,225 |
| | 1.0 μg/ml | 17 | 2,826 | 1,178 |
| EMS | 1.0 μg/ml | 3 | 9,760 | 8,112 |
| X-irr. | 250 R. | 7 | 6,453 | 4,805 |
| U.V.-irr. | 50 J/m$^2$ | 3 | 5,868 | 4,220 |
| BP | 1.0 μg/ml | 63 | 2,555 | 907 |
| Pyrene | 10 μg/ml | 83 | 1,577 | 0 |
| Phenanthrene | 10 μg/ml | 83 | 1,717 | 69 |
| DBS | 10 μg/ml | 83 | 1,525 | 0 |
| DMBA | 0.1 μg/ml | 4 | n.t. | — |
| Aflatoxin B1 | 0.1 μg/ml | 2 | 8,711 | 7,063 |
| | 0.01 μg/ml | 30 | 9,471 | 7,823 |
| | 0.001 μg/ml | 67 | 1,836 | 188 |
| 3 MCA | 1.0 μg/ml | 90 | 1,782 | 134 |
| 4 NQO | 1.0 μg/ml | 83 | 1,769 | 121 |

[a]Same experiment as described in FIG. 3.
[b]Fraction of cells surviving chemical treatment was determined by dividing the average number of treated cells per plate by the number of cells in the control plate.
[c]Filters containing $10^6$ cells were counted in toluene based scintillation fluid.

The reagents and other requirements for carrying out the assay of the present invention can be provided in kit form and the present invention relates also to such kits.

A typical kit for carrying out the assay comprises in combination the following, such kit being adequate for carrying out about ten individual assays:

1. Tester cells CO50, (I-188) CO60 (I-189) or other transformed Chinese hamster embryo cells. Cell lines will be provided in tissue culture bottles containing $1 \times 10^6$ cells/bottle. (A bottle which is filled with medium can be shipped by surface mail);
2. Fetal calf serum, 50 ml;
3. Nitrocellulose filters, 25 filters (0.4μ, 25 mm diameter);
4. 50×Denhardt 20 ml (1×Denhardt buffer 0.02% Ficol, 0.02% polyvinylpyrrolidone, 0.02% bovine serum albuminum);
5. $^{32}$P SV40 DNA labelled in vitro by nick translation. 10$^8$ counts per minute per kit at $1 \times 10^8$ counts per minute/μg DNA;
6. Sonicated denatured salmon sperm DNA, 5 ml of 10 mg/ml.

I claim:

1. A process for determining the carcinogenicity of chemical or physical agents, comprising:
    exposing tumor virus transformed cells, capable of endogenous viral DNA replication upon carcinogen exposure, to the agent to be tested; and
    determining whether the endogenous viral DNA content in such cells has been amplified,
    whereby a positive determination of viral DNA amplification is indicative of positive carcinogenicity of the tested agent.

2. A process in accordance with claim 1, wherein said tumor virus transformed cells comprise a cell line which is semi-permissive for viral replication, which cell line has been transformed by a tumor virus capable of transforming the cells of said cell line into cells capable of endogenous viral replication upon carcinogen exposure.

3. A process in accordance with claim 2, wherein said cell line comprises a Chinese hamster cell line.

4. A process in accordance with claim 3, wherein said Chinese hamster cell line comprises a Chinese hamster embryo cell line.

5. A process in accordance with claim 2, wherein said tumor virus is SV40.

6. A process in accordance with claim 1, wherein said tumor virus transformed cells comprise SV40 transformed Chinese hamster cells.

7. A process in accordance with claim 6, wherein said SV40 transformed Chinese hamster cell lines comprise the cell lines designated as CO50 (I-188) or CO60 (I-189).

8. A process in accordance with claim 1, wherein said step of determining whether the endogenous viral DNA content in such cells has been amplified comprises hybridization of the DNA content of said exposed cells with a labelled SV40 probe.

9. A process in accordance with claim 8, wherein said labelled SV40 DNA probe is a $^{32}P$ SV40 DNA probe.

10. A process in accordance with claim 9, wherein said hybridization is effected in situ.

11. A process in accordance with claim 1, wherein the agent to be tested is a suspected chemical carcinogen.

12. A process in accordance with claim 1, wherein the agent to be tested is a suspected physical carcinogen.

13. A process in accordance with claim 1, further including, after said determining step, the step of measuring the intensity of DNA amplification, thereby providing information about the degree of carcinogenicity of the tested agent.

14. A process for determining the carcinogenicity of chemical of physical agents, comprising
exposing SV40 transformed Chinese hamster cells to the agent to be tested; and
determining whether the endogenous SV40 DNA content in such cells has been amplified,
whereby a positive determination of SV40 DNA amplification is indicative of positive carcigenicity of the tested agent.

15. A process in accordance with claim 14, wherein said step of determining whether the endogenous SV40 DNA content in such cells has been amplified, comprises hybridization of the DNA content of said exposed cells, with a labelled SV40 probe.

16. A process in accordance with claim 15, wherein said hybridization is effected in situ.

17. A process in accordance with claim 14, wherein said SV40 transformed Chinese hamster cells comprise cell lines CO50 (I-188) or CO60 (I-189).

18. A kit for carrying out a process in accordance with claim 1, comprising a multi-container unit containing tester cells of SV40 transformed Chinese hamster cells; fetal calf serum; filters; Denhardt solution; $^{32}P$ labelled SV40 DNA; and sonicated denatured salmon sperm DNA.

* * * * *